United States Patent [19]

Judge et al.

[11] 4,236,076
[45] Nov. 25, 1980

[54] INFRARED ANALYZER

[75] Inventors: John F. X. Judge, Yorktown Heights; Victor G. Lipshutz, Tarrytown, both of N.Y.

[73] Assignee: Technicon Instruments Corporation, Tarrytown, N.Y.

[21] Appl. No.: 15,017

[22] Filed: Feb. 26, 1979

[51] Int. Cl.³ .............................................. G01J 1/00
[52] U.S. Cl. ................................... 250/347; 250/349
[58] Field of Search ............... 250/344, 343, 347, 349, 250/350, 358, 373; 356/447, 448

[56] References Cited

U.S. PATENT DOCUMENTS

| | | | |
|---|---|---|---|
| 3,641,349 | 2/1972 | Dahlin | 250/350 |
| 3,652,850 | 3/1972 | Briggs | 250/347 |
| 3,664,752 | 5/1972 | Hermieu | 356/448 |
| 3,776,642 | 12/1973 | Anson et al. | 356/448 |

Primary Examiner—Alfred E. Smith
Assistant Examiner—Janice A. Howell
Attorney, Agent, or Firm—S. P. Tedesco

[57] ABSTRACT

An infrared analyzer is described which analyzes constituents of a sample. The sample and/or reference signals are synchronously averaged to provide unisonous sample and reference values. This processing eliminates drift and signal noise from the measurements, thus providing a more sensitive and accurate characterization of the constituents of the sample.

11 Claims, 6 Drawing Figures

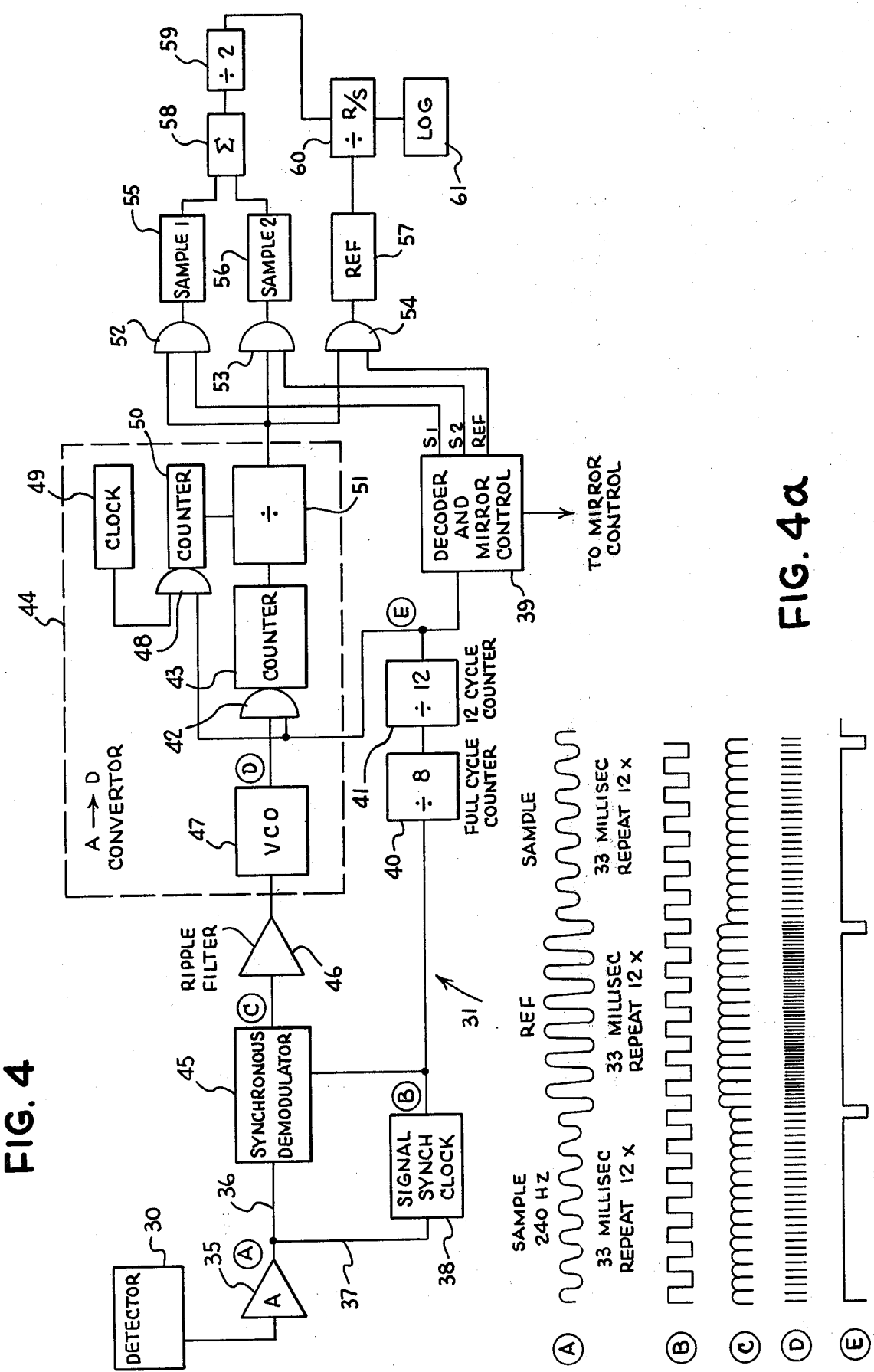

INFRARED ANALYZER

FIELD OF THE INVENTION

This invention relates to an infrared analyzer for analyzing the constituents of a sample and, more particularly, to an improved analyzer that is sensitive, accurate and of low cost.

BACKGROUND OF THE INVENTION

Infrared analyzers generally feature irradiating a food or organic sample with light in the near-infrared portion of the spectrum. The underlying principle of the analyzer is to photometrically measure the spectral variations in the reflected light, which variations are due to the spectrally selective absorption of the light by organic constituents in the sample. Light measurements conducted at several different wavelengths in the near infrared range will provide information determinative of the relative concentrations of the sample constituents as a result of their selectivity at the various wavelengths of light. A system of this general type is described in U.S. Pat. No. 3,776,642, issued to Anson et al. on Dec. 4, 1973.

The sample is usually measured concurrently with a reference to establish a proper measurement level and remove interferences peculiar to the system. Sample and reference measurements are often concurrently measured by means of a dual beam system, i.e., one beam directed at the sample and another beam directed at the reference. The necessity for measuring the sample and reference at the same time is to avoid or minimize errors due to drift in the measuring system.

Drift between sample and reference measurements cannot be tolerated due to the extreme accuracies demanded from this type of analyzer. Therefore, extreme care must be exercised to prevent a drift condition.

In some devices, a single beam is used to measure the sample and the reference. Drift between sample and reference measurements is eliminated in these systems by very rapidly switching the light beam between sample and reference. However, such systems require very complex and costly optics to provide this rapid light beam switching.

The present invention is for a single-beam system which is sensitive, less complex and of lower cost than previous analyzers.

The invention contemplates the utilization of a single beam which alternately irradiates the sample and reference at a relatively slow speed to eliminate costly and complex optics. Obviously, such a system cannot concurrently make both sample and reference measurements. Therefore, it is the purpose of this invention to process these non-concurrent measurements to provide sample and reference values which are effectively unisonous. This is accomplished by synchronously averaging the sample signal about the reference signal or vice versa.

The processing of the signals minimizes or eliminates the effects of drift and improves the signal-to-noise ratio.

Because the error in the signal is minimized electronically, a further advantage is realized, because light detectors having high tolerances, or temperature controls to prevent drift, are no longer required. This will additionally reduce the complexity and cost of the system.

SUMMARY OF THE INVENTION

The invention pertains to an analyzer for characterizing the constituents in a sample by reflectance techniques. The analyzer comprises a support for the sample, and a reference against which the sample is compared. Light is alternately and periodically directed to the sample and the reference by means of a tiltable mirror. Light reflected from the sample and the reference is utilized to generate a set of successive sample and reference signals. The set of signals comprises at least three signals, a triad of sample-reference-sample signals or reference-sample-reference signals. At least one type of signal in the set of signals is synchronously averaged to provide an unisonous output. The synchronous averaging of one or both types of signal provides sample and reference measurements which are effectively concurrently obtained. In other words, the differences related to drift in the signals is effectively minimized by or eliminated by the electronic synchronous averaging of the signals.

Summarizing, the invention therefore provides means for generating a set of successive signals responsive to the light reflected from sample and reference, and means to synchronously average at least one type of signal in the set, i.e., sample and/or reference. The synchronously averaged output is related to the other type of signal in the signal set so as to characterize constituents in the sample being analyzed.

It is an object of this invention to provide an improved infrared analyzer utilized for characterizing constituents of a sample;

It is another object of the invention to provide an infrared analyzer which is sensitive, accurate and of low cost;

It is still another object of this invention to provide an infrared analyzing system for characterizing constituents of a sample, whose output signals are substantially free of drift, and have an improved signal-to-noise.

These and other objects of this invention will be better understood and will become more apparent with reference to the following detailed description taken in conjunction with the accompanying drawings in which:

BRIEF DESCRIPTION OF DRAWINGS

FIG. 4 is an electrical diagram of the electronics for processing the signals generated in the apparatus shown in FIG. 1;

FIG. 4a is a diagram of the signal wave forms generated at various points in the electrical circuit depicted in FIG. 4.

DETAILED DESCRIPTION

Figure 1:
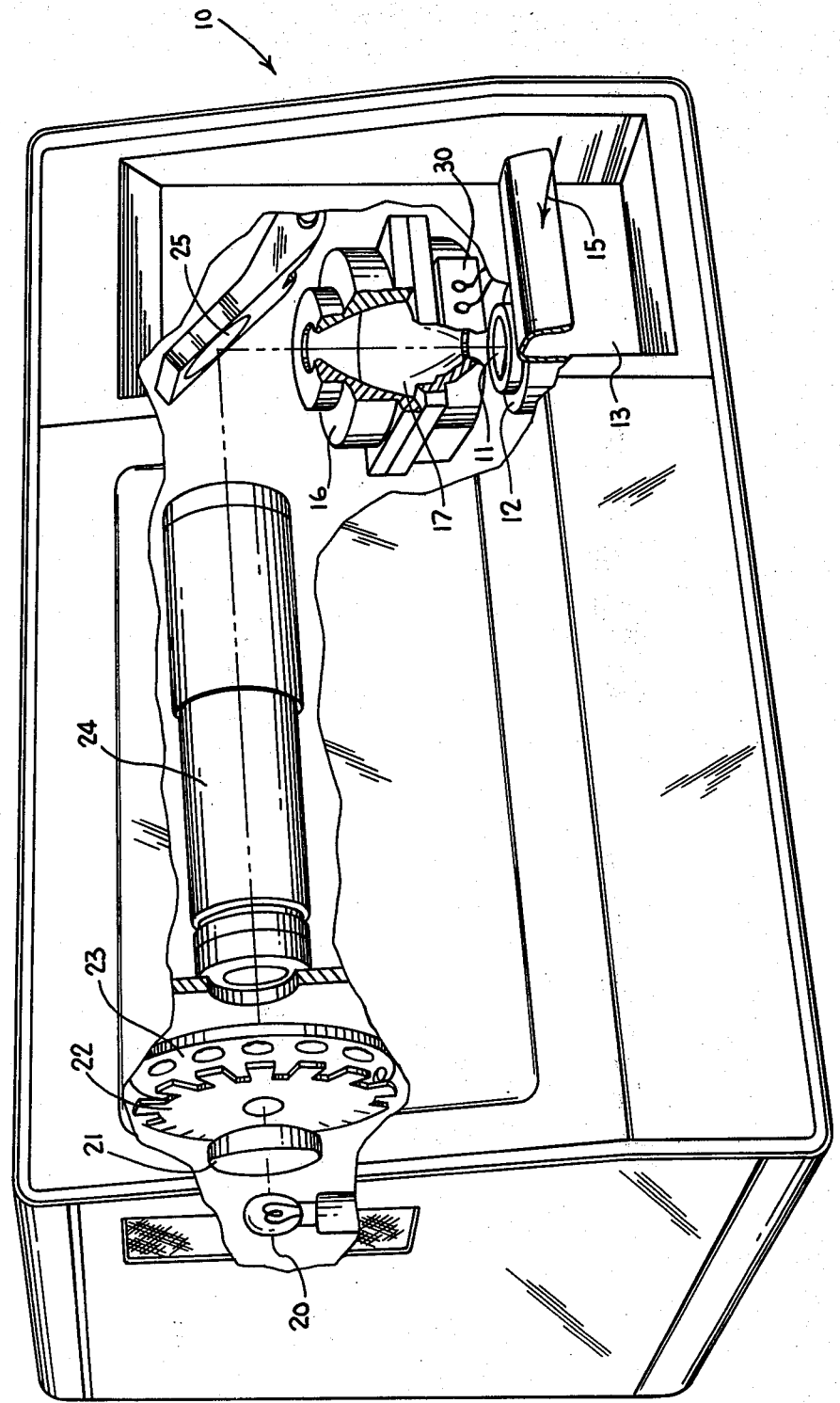
FIG. 1 is a cutaway perspective view of the apparatus of the invention.
Figure 2:
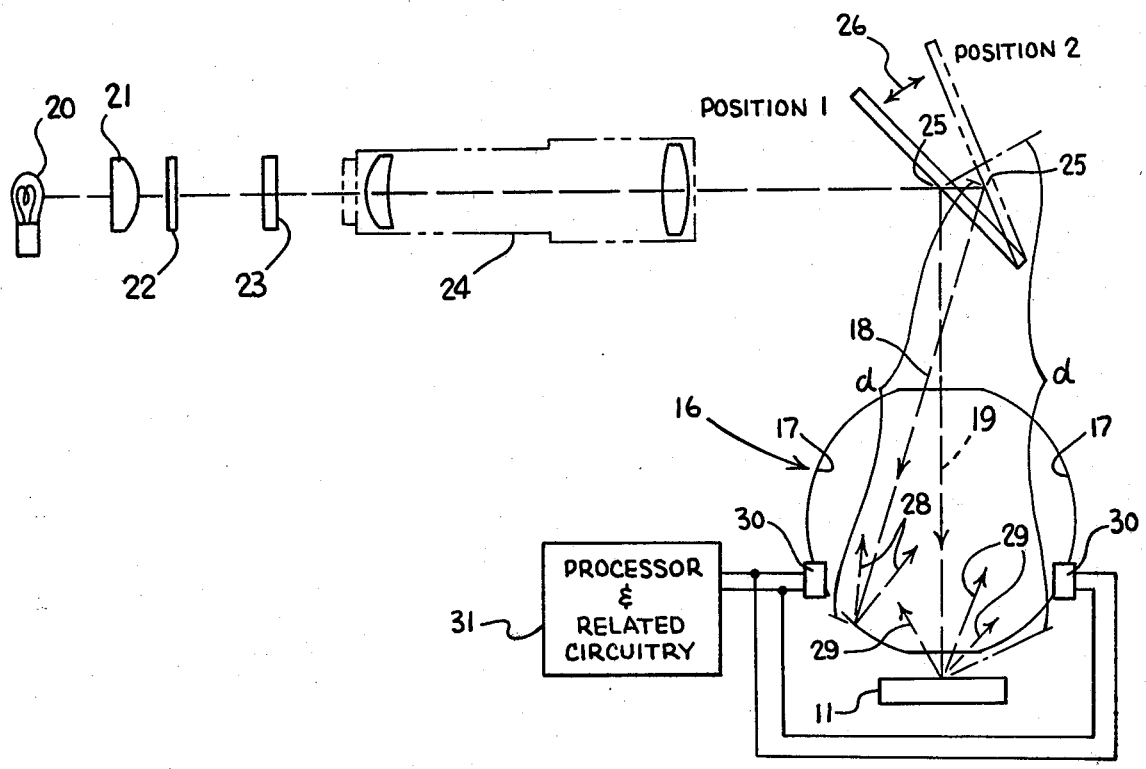
FIG. 2 is a schematic view of the apparatus shown in FIG. 1.

For the sake of brevity, like designations will be used throughout the descriptive figures for similar elements. FIGS. 1 and 2 should be viewed together with regard to the following description.

Now referring to FIG. 1, an infrared analyzer 10 is shown, wherein a sample 11 to be analyzed is supported in a cup 12, which is further carried upon a slidable tray 13. The tray 13 has a handle 14 for slidably moving (arrow 15) the sample cup 12 beneath a light integrating chamber 16, shown in a cutaway view.

It is the purpose of chamber 16 to integrate reflected light 29 (FIG. 2) from the sample 11 in order to characterize the constituents of the sample 11. Light for this measurement is obtained from an infrared light generating incandescent bulb 20. The light from bulb 20 is focused by lens 21, and then passed through a chopping wheel 22. The chopping wheel 22 has as its purpose to provide a pulsed or periodic beam to the sample 11 and chamber 16, respectively. The pulsed beam then intersects a filter wheel 23 which is indexed in controlled fashion to provide a beam having successive monochromatic wavelengths. Various wavelengths are directed at sample 11 via wheel 23, because the different constituents in the sample selectively absorb the light at different wavelengths. It is this selective absorption, or lack of reflectivity of the light from the sample 11 at these various wavelengths, which characterizes the particular types of constituents therein contained. The intensities of the reflected light at the various wavelengths will also characterize the amounts of each constituent under analysis. The light leaving the filter wheel 23 is passed through a collimator 24, and is directed upon a mirror 25. The mirror is movably mounted (arrow 26) between two respective positions "1" and "2", as shown in FIG. 2.

In position "1", the light beam from collimator 24 is directed by mirror 25 along light path 19 towards sample 11. When the mirror 25 is in position "2", the light beam from collimator 24 is directed along light path 18 towards the inner surface 17 of chamber 16. The inner surface 17 of chamber 16 is coated to diffuse, or otherwise integrate, the light which is captured. This diffusing surface 17 also acts as an internal reference against which the sample is compared. When the light from mirror 25 is directed towards the sample 11, as shown by light path 19, reflected light 29 from the sample 11 will enter chamber 16 and be integrated by diffusing surface 17. When the light from mirror 25 is directed towards reference surface 17 via light path 18, the reflected light 28 of the reference is integrated. The reference light energy established a level of reference for the measured light energy of the sample.

Two electrically coupled detectors 30 (only one detector shown in FIG. 1) are symmetrically placed in chamber 16 to sense the light energy, and convert this energy into sample and reference-type signals that are then processed by circuitry 31. Circuit 31 will be described hereinafter with respect to FIGS. 4 and 4a.

The mirror 25 is mounted in such a way that the light path distances "d" from the mirror 25 to the reference and samples, along beams 18 and 19, respectively, are equal. The equal distances "d" will eliminate radiant errors from the light measurement. To achieve this condition, the mirror 25 must actually translate as well as rotate between positions "1" and "2". A motorized cam control (not shown) is used to move the mirror. The present light directing device was chosen for its simplicity, and other devices such as beam splitters may be used consistent with the inventive purpose.

The alternating speed of the light directing mirror is purposely chosen to be slow to achieve simplicity in optical design. However, because of its design, the utilization of an internal reference was chosen to allow for a quicker switching between sample and reference. However, drift will, nevertheless, occur between adjacent sample and reference signals.

In theory, it is desirable to measure the reflected light from the sample and reference at the same time to avoid drift. However, this is usually only achievable with a dual beam, or other more complicated systems.

The present invention, therefore, contemplates switching the light beam several times between sample and reference to obtain a generally odd number of successive sample and reference signals from detectors 30. Generally speaking, at least three signals are obtained in either a sample-reference-sample triad or, alternately, a reference-sample-reference triad. The bracketing signals, when electronically averaged, will have a value which will be unisonous with the bracketed signal.

Figure 3A:
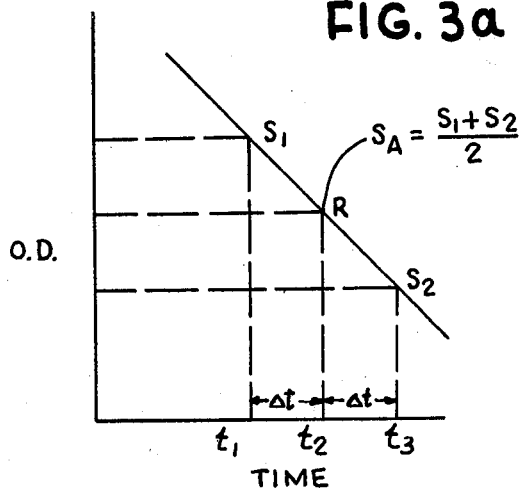
FIGS. 3a and 3b are graphs of optical density versus time for the sample and reference signals generated in the apparatus of FIG. 1.
Figure 3B:
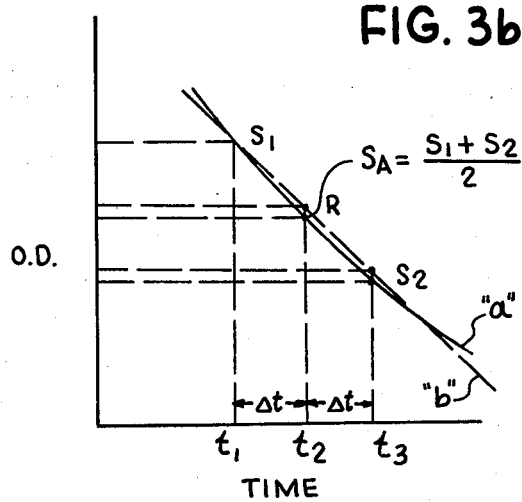

As a means of illustrating the invention, reference is now made to FIGS. 3a and 3b. Assuming that the drift between successive signals is linear, the sample-reference-sample signals (expressed as optical density O.D.) are depicted as linearly displaced in FIG. 3a. The first sample signal "$S_1$" is taken at time $t_1$. After a given time interval $\Delta t$, the reference signals "R" is obtained at time $t_2$. After another equal or fixed time interval $\Delta t$, a second sample signal "$S_2$" is taken at time $t_3$.

It will be observed that if the two signals "$S_1$" and "$S_2$" are synchronously averaged, the resulting value of the synchronously averaged sample signals, "$S_A$" is that sample value which would otherwise have been taken concurrently with the reference signal "R". In other words, the synchronous averaging of the bracketing signals will result in a signal which would have been made at the same time as the bracketed signal. Naturally, if more than three signals (i.e., five signals $S_1$, $R_1$, $S_2$, $R_2$, $S_3$, by way of example) are considered as part of the operating set, then the sample signals $S_1$, $S_2$, and $S_3$ and reference signals $R_1$ and $R_2$ would need to be respectively synchronously averaged to get concurrent values.

Also, if the reference signal "R" is the bracketing signal in a triad of R-S-R signals, then reference signals will be synchronously averaged about the bracketed sample signal "S".

FIG. 3b illustrates a non-linear drift (curve "a") between signals "$S_1$", "$R_1$", and "$S_2$", respectively, as compared to a linear drift (curve "b"). Again, the correction provided by synchronous averaging signals "$S_1$" and "$S_2$", provides an almost concurrent value "$S_A$" with that of the reference signal "R".

In almost all cases, the synchronous averaging of the bracketing signals in the triad set will provide an improvement in the processed signal, such that drift will be effectively eliminated or minimized. In addition, the processed signal will have an improved signal-to-noise ratio.

Now referring to FIGS. 4 and 4a, the electrical processing of the signals is shown by the block circuit diagram 31. Signals coming from the detectors 30 are fed to an amplifier 35, whose signal output is shown by pulse train "A" of FIG. 4a. The sample-reference-sample signals shown, comprise twelve (33-milliseconds) samplings of each of the sample and reference measurements. This output is then fed along lines 36 and 37, respectively. The signals fed along line 37 are introduced to a clock 38 for synchronizing the processing of the signals with the mirror control 39. The output clock signal is shown in FIG. 4a as pulse train "B". The pulses "B" are further conditioned by the divider circuits 40 and 41, respectively, to provide one pulse at the beginning of every sample or reference cycle as depicted by pulse train "E" in FIG. 4a. These periodic pulses are a feedback control to insure that the mirror will alternate at the proper time between positions "1" and "2", (FIG. 2). Pulses "E" are also fed to an AND gate 42 of the counter 43 of the analog-to-digital converter 44. This functions to synchronize the electrical signals in line 36.

Signals "A" from amplifier 35 are fed to a synchronous demodulator 45 to produce the signal shown as "C" in FIG. 4a. This demodulated signal is fed to a ripple filter 46, and then to a voltage control oscillator 47. The voltage control oscillator 47 is part of the analog-to-digital converter 44, and provides a train of output pulses depicted as "D" in FIG. 4a. The pulses "D" will be passed to counter 43, when the AND gate 42 is enabled by the aforementioned "E" pulse train.

The purpose of the analog-to-digital converter 44 is to convert the oscillating pulses into a single power level signal for the sample and reference measurements An AND gate 48, which is fed by an external clock 49 also is enabled by pulses "E". This AND gate 48 actuates counter 50. Both counter 43 and counter 50 feed to a divider 51, to produce a single power level signal for each sample and reference measurement.

The averaging of the sample signals "$S_1$" and "$S_2$" as graphically illustrated in FIG. 3a is accomplished by sequentially passing the power level signals to three AND gates 52, 53, and 54, respectively. The decoder and mirror circuit 39, which is influenced by pulse train "E", will periodically enable each respective AND gate 52, 53, and 54, in turn, according to the duration of the sample and reference signals. The respective AND gates 52, 53, and 54 will pass the power level signals "$S_1$", "$R_1$" and "$S_2$" to an appropriate location in memory depicted by blocks 55, 56, and 57, respectively.

The summing circuit 58 will sum both sample signals "$S_1$" and "$S_2$", and the divider circuit 59 will synchronously average these signals.

A ratio $R/S_A$ of the synchronously averaged sample "$S_A$" and the reference signal "R" is provided by circuit 60, and circuit 61 provides the log 10 of the ratio $R/S_A$.

This log 10 $R/S_A$ value is equal to the optical density (O.D.) of the sample at a given wavelength.

The percentage of a specific chemical or biological components of the sample 11 (FIGS. 1 and 2) is determined or characterized by summing the optical densities at various wavelengths of light:

$$X_c = F_1 O.D.\lambda_1 + F_2 O.D.\lambda_2 + F_3 O.D.\lambda_3 + \ldots \text{etc.}$$

where: $X_c$ is a concentration characteristic of the constituent of the sample; $O.D.\lambda_1$, $O.D.\lambda_2$, and $O.D.\lambda_3$ are the optical densities at different wavelengths of light; and $F_1$, $F_2$, and $F_3$ are calibration values established from standard constituent data.

Having thus described the invention, what is sought to be protected by Letters Patent is presented by the appended claims.

What is claimed is:

1. An analyzer for characterizing a particular constituent in a sample, comprising:
    a support for said sample;
    a reference against which said sample is compared;
    means responsive to light alternately to said sample and said reference;
    means responsive to light alternately reflected from said sample and said reference for generating a set of successive sample and reference signals, said set comprising an odd number of at least three signals, the time interval between successive ones of said signals being equal;
    means coupled to said generating means for synchronously averaging one of said signals in said set to provide a synchronous output; and
    means coupled to said synchronous averaging means for relating said synchronously averaged output to the other of said signals in said set, so as to characterize said constituent in said sample.

2. The analyzer of claim 1, wherein said signal set comprises a sample-reference-sample triad, and said averaging means being operative to provide a synchronously averaged signal of said sample signals.

3. The analyzer of claim 1, wherein said signal set comprises a reference-sample-reference triad, and said averaging means being operative to provide a synchronously averaged signal of said reference signals.

4. The analyzer of claim 1, wherein said generating means comprises a light integrating chamber, and further wherein said reference forms an integral part of said chamber.

5. The analyzer of claim 4, wherein said chamber has inner walls, and said inner walls of said chamber include said reference.

6. The analyzer of claim 1, wherein said periodic light directing means comprises an infrared light source for providing a beam of light, a chopper disposed adjacent said light source for chopping said beam of light, a filter means disposed adjacent said chopper for filtering said chopped light beam to provide a monochromatic light beam, and a movably mounted mirror which intersects said light beam and alternately directs said beam of light to said sample and said reference.

7. The analyzer of claim 6, wherein said movably mounted mirror is positioned to direct light an equal distance to both said sample and said reference.

8. The analyzer of claim 6, wherein said filter means is comprised of a wheel of filters which is indexed to provide monochromatic light of different wavelengths.

9. The analyzer of claim 1, wherein said synchronous averaging means comprises an analog-to-digital converter for converting said signals of said set of signals into individual power level values, memory means coupled to said analog-to-digital converter for storing said individual power level values, and summing and division circuitry coupled to said memory means for synchronously averaging at least two of said power level values.

10. The analyzer of claim 1, wherein the means for relating the synchronously averaged output includes a means for providing a ratio of said synchronously averaged output and said other of said signals, and means for providing the log of the ratio to obtain an optical density value which is characteristic of said constituents in said sample.

11. The analyzer of claim 1, wherein said averaging means will synchronously average said sample and said reference signals in said set, when said set comprises more than three signals.

* * * * *

UNITED STATES PATENT AND TRADEMARK OFFICE
CERTIFICATE OF CORRECTION

PATENT NO. : 4,236,076
DATED : November 25, 1980
INVENTOR(S) : JOHN F. X. JUDGE and VICTOR G. LIPSHUTZ It is certified that error appears in the above–identified patent and that said Letters Patent are hereby corrected as shown below:

In Column 5, lines 63 and 64, cancel: "means responsive to light alternately to said sample and said reference;"

and insert -- means for periodically directing a light beam alternately to said sample and said reference; -- .

Signed and Sealed this

Eighteenth Day of August 1981

[SEAL]

Attest:

Attesting Officer

GERALD J. MOSSINGHOFF

Commissioner of Patents and Trademarks